United States Patent [19]
della Valle et al.

[11] Patent Number: 4,897,381
[45] Date of Patent: * Jan. 30, 1990

[54] ORGANIC AMIDE COMPOUNDS DERIVED FROM NITROGENOUS LIPIDS

[75] Inventors: Francesco della Valle, Padua; Aurelio Romeo, Rome, both of Italy

[73] Assignee: Fidia S.p.A., Abano Terme, Italy

[*] Notice: The portion of the term of this patent subsequent to Jul. 12, 2005 has been disclaimed.

[21] Appl. No.: 209,490

[22] Filed: Jun. 21, 1988

Related U.S. Application Data

[60] Division of Ser. No. 807,841, Dec. 11, 1985, Pat. No. 4,757,053, which is a continuation of Ser. No. 404,706, Aug. 3, 1982, abandoned.

[30] Foreign Application Priority Data

Aug. 3, 1981 [IT] Italy ............................... 49031 A/81

[51] Int. Cl.$^4$ ....................... C07D 473/08; C07F 9/65; A61K 31/52
[52] U.S. Cl. .......................................... 514/25; 514/81; 514/258; 536/17.4; 536/17.9; 536/53; 544/244; 544/262
[58] Field of Search ............... 544/244, 262; 536/17.9, 536/17.4, 81, 18, 53; 514/258

[56] References Cited

FOREIGN PATENT DOCUMENTS 0072286 2/1983 European Pat. Off. .

Primary Examiner—Mary C. Lee
Assistant Examiner—Richard A. Sharpe
Attorney, Agent, or Firm—Birch, Stewart, Kolasch & Birch

[57] ABSTRACT

Organic amide compounds of the formula

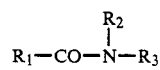

wherein $R_1$—CO is a residue of a carboxylic acid with the proviso that the carboxylic acid is not a natural fatty acid normally bound to nitrogen of nitrogenous lipids, $R_2$ is a hydrogen atom, a $C_{1-7}$ alkyl group, or a $C_{4-7}$ cycloalkyl group, and $R_3$-$N$ is a residue of a nitrogenous lipid. The compounds are useful in increasing or stimulating the in vivo biological activity of in vitro biologically active carboxylic acids.

13 Claims, No Drawings

ORGANIC AMIDE COMPOUNDS DERIVED FROM NITROGENOUS LIPIDS

This application is a divisional of application Ser. No. 807,841, filed on Dec. 11, 1985, which is a Continuation of Ser. No. 404,706, filed on Aug. 3, 1982, now abandoned.

BACKGROUND AND FIELD OF THE INVENTION

The present invention relates to novel organic amide compounds, procedures for preparing the compounds, pharmaceutical compositions containing the same and methods for using the compounds. These novel organic amides are primarily comprised of a carboxylic acid moiety and a nitrogenous lipid moiety.

Numerous compounds are known to be active in vitro and yet exhibit little or no activity in vivo. In particular, numerous carboxylic acids are known to be important in the actions of the peripheral and central nervous systems and are active in vitro but are either non-active or only slightly active in vivo. Gamma-aminobutyric acid (GABA), for example, is known to be active on the central nervous system in vitro and has been suggested as a possible inhibitory transmitter (Louis S. Goodman and Alfred Gilman, The Pharmacological Basis of Therapeutics, 4th Ed., p. 429 (1970)). However, GABA has been found to be ineffective when administered in vivo as measured by convulsion tests in mice.

The present inventors have found that compounds of the formula I, prepared by combining a carboxylic acid, such as GABA, with a nitrogenous lipid, such as a phospholipid or sphingosine, provide amide compounds which are active in vivo, exhibiting activities far superior to that of the corresponding carboxylic acid or lipid compounds administered alone. For example, the amide of GABA with a sphingosine provides a compound which is far more active in vivo than is GABA alone. Similarly, lysergic acid, dihydrolysergic acid and isolysergic acid are essentially inactive when administered alone, but when combined with a sphingosine provide compounds of the formula I which have significant in vivo activity as measured by hypoprolactinemic effects in rats.

The significantly improved pharmacological properties of the compounds of formula I are thought to result from the ability of these compounds to penetrate the hematoencephalic barrier and/or reach the peripheral organs far better than the carboxylic acid compounds alone. This ability of the compounds of the present invention favors the interaction between the biologically active compound, such as the carboxylic acid, and the situs of the specific interactions present in the membranes.

Hence, the compounds of the present invention are useful for enhancing or increasing the in vivo biological activity in vitro biologically active carboxylic acids as well as stimulating the in vivo biological activity of in vitro biologically active carboxylic acids which have little or no in vivo activity.

OBJECTS AND SUMMARY OF THE INVENTION

It is another object of the present invention to provide compounds which permit the in vivo activity of other compounds which are known to be biologically active in vitro.

It is a further object of the present invention to provide a process for preparing the novel amide compounds.

It is still another object of the present invention to provide methods for use the compounds of the present invention as therapeutic agents.

It is a still further object of the present invention to provide pharmaceutical compositions which comprise at least one of the novel amide compounds as an active ingredient.

These and further objects of the present invention are accomplished by providing the novel amide compounds of formula I and pharmaceutical compositions containing the same. These amide compounds comprise a carboxylic acid moiety and a nitrogenous lipid moiety and are pharamcologically active in vivo due to the activity of the corresponding carboxylic acid but exhibit activity far superior than results from in vivo administration of the carboxylic acid alone.

DETAILED DESCRIPTION OF THE INVENTION

The novel organic amide compounds of the present invention are represented by the formula I

wherein $R_1$—CO is a residue of an organic carboxylic acid which has a pharmaceutical or biological activity with the proviso that the carboxylic acid is not a natural fatty acid normally bound to nitrogen of nitrogenous lipids, $R_2$ is a hydrogen atom or one of a group of hydrocarbons and $NR_3$ is a residue derived from a nitrogenous liquid. Natural fatty acids normally bound to nitrogen in nitrogenous lipids are described in, for example, Wiegandt, Adv. in Lipid Res., Vol. 9, pp. 249-288, Ed. by Paoletti and Kritchezsky (Academic Press, 1971) and Ansell and Hawthorne, Phospholipids, Biochem. Biophys. Acta. Library, Vol. 3, pp. 420-425 (Elsevier Pub. Co., 1964).

The $R_1$—COOH acids which give rise to the $R_1$—CO residue are primarily those acids which are fundamentally important to the peripheral and central nervous systems, such as lysergic, isolysergic, dihydrolysergic, 2-bromolysergic, 2-bromo-dihydrolysergic, 1-methyllysergic, 1-methyldihydrolysergic, 1-methyl-2-bromolysergic, 1-methyl-2-bromodihydrolysergic, gamma-aminobutyric, valproic (2-propylpentanoic), trimethoxybenzoic, nicotinic, isonicotinic, picolinic and theophyllineacetic acids. These acids have the common pharmaceutical characteristic of being active in vitro but nonactive or only slightly active in vivo.

$R_2$ may be a hydrogen atom or a hydrocarbon, especially a saturated aliphatic hydrocarbon or a saturated cycloaliphatic hydrocarbon group; for example an alkyl having from 1 to 7 carbon atoms such as butyl, isobutyl, tertiarybutyl, propyl, isopropyl, ethyl, and methyl or a cycloalkyl having from 4 to 7 carbon atoms, such as cyclobutyl, cyclopentyl, cyclohexyl, and cycloheptyl.

The —N—$R_3$ residue is derived from a nitrogenous lipid, especially from phospholipids and sphingolipids. Phospholipids, natural products that can be extracted from bovine brain tissue, are chemically derived from L-α-glycerophosphoric acid. (Lees, M. B., Met. Enzymol, Vol. 3, pp. 328–345 (1957); Bigon et al, G. Brit. J. Pharmacol., Vol. 67, pp. 611–619 (1979); Spanner, Form and Function of Phospholipids, Ed. by Ansell et al, Biochem. Biophys. Acta. Library, Vol. 3, pp. 43–65 (1973)). The two major phospholipid groups which are utilized are the phosphatidylethanolamines (II) and the phosphatidylserines (III) represented by the following structures:

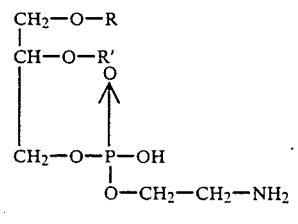

wherein R and R' represent a hydrogen atom or the residue of an organic carboxylic acid, especially, the residue of a saturated or unsaturated fatty acid.

Sphinolipids are natural products extracted, in particular, from animals and vegetables and contain an amino-alcohol moiety (Dawson, Form and Function of Phospholipids, Ed. by Ansell et al, Biochem. Biophys. Acta. Library, Vol. 3, pp. 104–105 (1973); Kaller, Biochem. Zeitschrift, Vol. 334, pp. 451–456 (1961); Sweeley et al, J. Lipid, Res., Vol. 1, pp. 40–47 (1959); Radin, Lipids, Vol. 9, pp. 358–360 (1970)). Especially preferred sphinogosines are those having an average of 12 to 22 carbon atoms.

The sphingolipid derivatives which permit the preparation of the compounds (I) of the present invention contain a sphingosinic residue and contain a free sphingosine —NH$_2$ group. Principally these are:

Sphingosine represented by the formula:

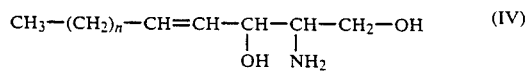

wherein n may be from 6 to 16,

Dihydrosphingosine represented by the formula:

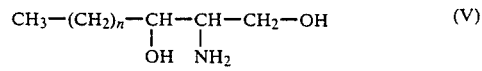

wherein n may be from 8 to 18,

Psychosine or galactosylsphingosine represented by the formula:

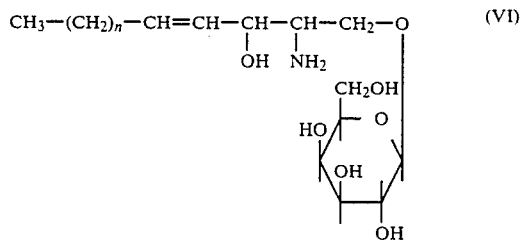

wherein n may be from 6 to 16,

Dihydropsychosine represented by the formula:

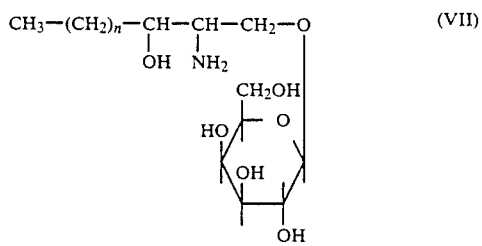

wherein n may be from 8 to 18,

Phosphorylcholine sphingosine or lisosphingomyelins represented by the formula:

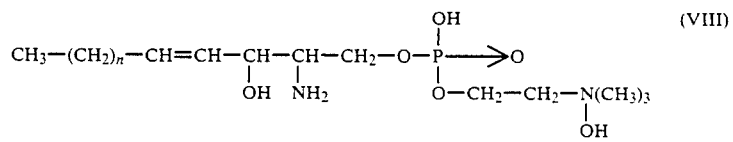

wherein n may be from 6 to 16,

Phosphorycholine—dihydrosphingosine, or lisodihydrosphingomyelines represented by the formula:

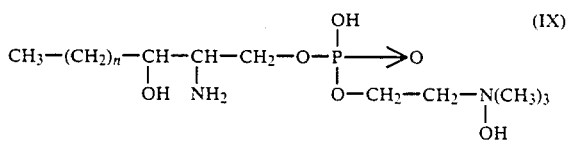

wherein n may be from 8 to 18,

Phytosphingosine represented by the formula:

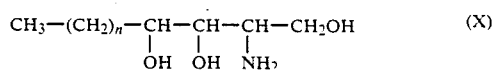

wherein n may be from 11 to 15, and all other sphingolipids which through hydrolysis are capable of releasing an amine (—NH$_2$) group, such as is indicated below by the sphingomyelin formula XI:

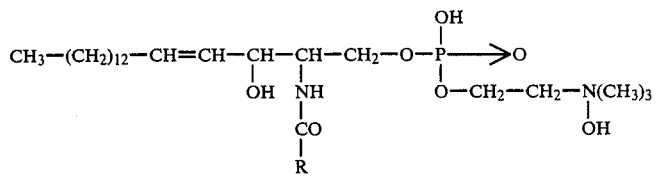

Preparation Procedures

The organic amides (I) according to the present invention can be prepared according to a variety of preparation methods under conditions which prevent the esterification of the free hydroxy acid. Of all the methods which have proved to be particularly appropriate, the following are most preferred.

1. The reaction between the $R_1CON_3$ azides (corresponding to the $R_1$—COOH acid) and the nitrogenous lipid derivatives. The preparation of the $R_1CON_3$ azides can be realized by utilizing one of the known methods.
2. The acylimidazole preparation method comprising reacting the $R_1COOH$ acid with N, N'-carboxydiimidazole, followed by the reaction of the thus produced acylimidazole with the nitrogenous lipid.
3. The mixed anhydride preparation method comprising reacting the $R_1COOH$ acid and trifluoroacetic acid anhydride to form a mixed anhydride and then reacting the mixed anhydride with the nitrogenous lipid.
4. Preparing the acid chloride of the $R_1COOH$ acid followed by reacting the acid chloride with the nitrogenous lipid.
5. Direct reaction between the $R_1COOH$ acid and the nitrogenous lipid in the presence of a carbodiimide (for example dicyclohexylcarbodiimide, benzylisopropylcarbodiimide or benzylethylcarbodiimide) or another substance similar to 1-hydroxybenzotriazole.
6. Direct condensation from heating the $R_1COOH$ acid with the nitrogenous lipidic derivatives.
7. Direct reaction between the methyl ester of the $R_1COOH$ acid and the nitrogenous lipidic derivative; this reaction is favored by heating.
8. Preparation of an ester by the reaction between an $R_1COOH$ acid and a phenol (for example, paranitrophenol) followed by the reaction of the ester with the nitrogenous lipid. The ester preparation between the acid and a phenol can be realized by using one of the known methods.

In the preparation of the products described in formula (I) derived from gamma-aminobutyric acid, the method preferably used is that consisting of the initial preparation of a gamma-aminobutyric derivative where the amine group is attached to a protective group, as for example, a phthaloyl or benzyloxycarbonyl group. The derivative thus prepared is then further condensed with the nitrogenous lipid using one of the reactions previously described. The protective group is then eliminated by means of an appropriate reaction and the product (I) is thus obtained. For example, if the protective group is phthaloyl, this group could be eliminated by hydrazinalysis.

The compounds of formula I, wherein the $R_1$—COOH acid contains a basic group (for example, gamma-aminobutyric, nicotinic, lysergic or dihydrolysergic acid), can be salified with therapeutically used acids such as: hydrochloric, hydrobromic, methanesulphonic and malic acids.

As described above, according to the present invention, numerous compounds, particularly carboxylic acids, can be combined with nitrogenous lipids to produce amine compounds which are pharmaceutically active in vivo. Although not limiting, the following examples illustrate the products, preparation procedures and pharmaceutical preparations of the present invention.

EXAMPLE 1

Product 1

Gamma-aminobutyrylsphingosine amides of the formula:

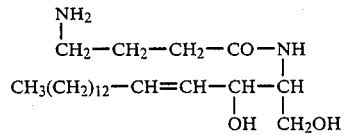

a. A gamma-phthalmid-butyryl-sphingosine-amide (Product 1a) is prepared as follows: 5.7 g of sphingosine (obtained from the sphingolipids present in the bovine brain and corresponding to a sphingosine $C_{18}$) are treated with 50 ml of absolute ethanol. 8.9 g of the para-nitrophenylester of gamma-phthalmidbutyric acid (prepared according to: J. Org. Chem. 27, 684–696, 1962) are added to the solution.

The solution is then heated and left to precipitate for 2 hours and the solvent is vacuum separated. The residue is mixed with 500 ml of a methylene chloride ethanol mixture (4:1). The organic solution is washed with an aqueous solution of sodium carbonate and then with water. The organic solution is dried on sodium sulphate, filtered and the solvent is then vacuum separated.

The residue crystallizes from methylene chloride—n-hexane, M.P. 97° C., yield 7.3 g.

Thin layer chromatography (silica gel) using a eluent mixture of methylene chloride:ethyl acetate:methanol, 70:30:10, indicates that it is a single compound with Rf of 0.4.

Elementary analysis gives the following results (%):
C 70.20; H 8.94; N 5.61
For $C_{30}H_{46}N_2O_4$, theoretical % calculated is
C 70.00; H 9.01; N 5.44 b. 5.14 g of the gamma-phthalamid-butyryl sphingosineamide (Product 1a) are treated with 30 ml of absolute ethanol; 20 ml of an ethanolic solution of 1 Molar hydrazine are added and heated and allowed to precipitate for 2 hrs. The solvent is then evaporated in a vacuum and 50 ml of acetic acid (2 Normal) is added to the residue and heated for 10 minutes at 50° C. The mixture is left to cool to room temperature and filtered. The filtered solution is concentrated in vacuum and a water solution of NaOH (2N) until a clearly alkaline pH is obtained.

The aqueous phase is extracted with a mixture of methylene chloride: ethanol (4:1). The organic solution is dried on sodium sulphate, which is filtered and evaporated. The residue crystallizes from tertiarybutylmethyl ether, and gamma-amino-butyryl-sphingosine amides (Product 1) M.P. 87° C., are thus obtained (yield 3.1 g).

Thin layer chromatography (silica gel) using an eluent mixture formed by chloroform:methanol:water:ammonia concentrated aqueous solution (70:35:5:1) indicates that the Product 1 is a single compound with Rf of 0.16.

Elementary analysis gives the following results (%):
C 68.56; H 11.50; N 7.37
For $C_{22}H_{44}N_2O_3$, theoretical % calculated is
C 68.70; H 11.53; N 7.28

EXAMPLE 12

Products 2.1 and 2.2

Isolisergylsphingosine amides of the formula:

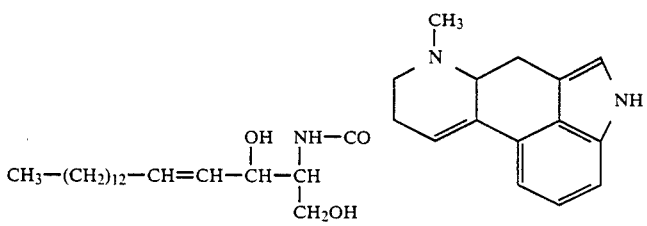

and lysergylsphingosine amides, an isomer from the formula 2.1, of the formula:

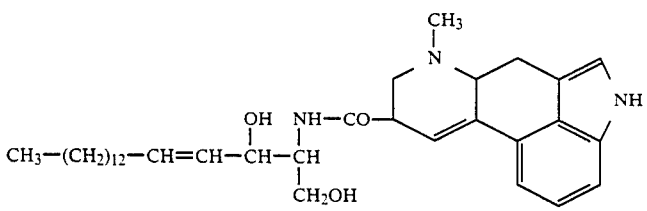

6.7 g of D-lysergic acid are treated with 400 ml of dimethylformamide (DMF) (this reaction is conducted taking care to work away from light); the lysergic acid gradually forms a solution. 4.45 g of N,N'-carbonyl diimidazole dissolved in 125 ml of DMF are added to the solution and the kept at room temperature for 2 hours. 8.25 g of sphingosine (obtained from the sphingolipids present in the bovine brain and corresponding to a sphingosine $C_{18}$) are added and the mixture is maintained at room temperature for 24 hours.

DMF is evaporated in vacuum and the residue is treated with 1000 ml of ethyl acetate, the suspension is filtered and the organic solution washed with 5M of ammonia and then with water. The organic solution is dried o sodium sulphate, and then filtered and evaporated, thus obtaining a residue.

The residue is then chromatographically fractionated, separating the two compounds: Product 2.1; Product 2.2.

a. Product of 2.1-Isolysergylsphingosine-amide

Chromatography on silica gel plates using an eluent mixture of ethyl acetate: methanol, 80:20, indicates that it is a single compound with Rf 0.74. Evaluation of the specific rotating power is carried out in methanol solution (1%) using a ldm polarimetric tube- result is $(\alpha)_D = 235°$ Elementary analysis gives the following results:
C 74.16; H 9.55; N 7.78
For $C_{34}H_{51}N_3O_3$ % calculated is
C 74.27; H 9.35; N 7.64 b. Product 2.2-Lysergylsphingosine-amide (Product 2.1)

(Product 2.2)

(crystallizes from acetone, M.P. 139° C.)

Chromatography on silica gel plate using an eluent mixture of ethyl acetate: methanol, 80:20, indicates that it is a single compound with Rf 0.30. Evaluation of the specific rotary power is carried out in 1% chloroform using a 1 dm polarimetric tube-result is $(\alpha)_D = +3$ Elementary analysis gives the following results (%):
C 74.10; H 9.42; N 7.80
For $C_{34}H_{51}N_3O_3$ theoretical % calculated is
C 74.27; H 9.35; N 7.64

EXAMPLE 3

Product 3 a. Dihydrolysergylsphingosine amide of the formula:

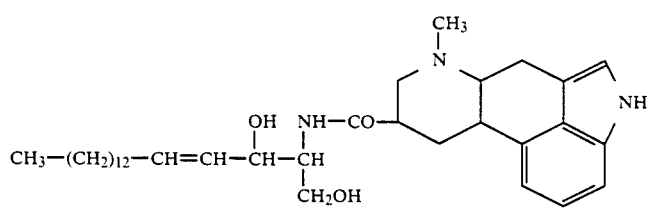

2.7 g of dihydrolysergic acid (prepared from catalytic hydrogenation of the lysergic acid) and 2.7 g of 1- hydroxybenzotriazole are added to 100 ml of chloroform. The mixture, under continual agitation, is brought to 30° C., after which 3 g of sphingosine (obtained from the sphingolipids present in the bovine brain and corresponding to a sphingosine $C_{18}$) and 2 g of dicyclohexylcarbodiimide are added.

The mixture is heated and allowed to precipitate for 1 hour, brough to room temperature and then 25 ml of ethanol are added.

The organic solution is washed with 5M ammonia and then with water. The organic solution is vacuum dried, thus obtaining a residue and solubilized in 30 ml of methanol.

The methanolic solution is brought to 0°, thus precipitating the dicyclphexylurea; the suspension is filtered and the solvent is eliminated from the filtered substance by vacuum. The residue is solubilized by heating with 45 ml of acetone. While cooling, the dihydrolysergylsphinogosine amides crystallize, M.P. 206° C., yield 3.8 g.

Thin layer chromatography (silica gel) using an eluent mixture of methylene chloride:ethyl acetate:methanol 60:30:15, indicates that it is a single compound with Rf of 0.25.

Evaluation of the specific rotary power is carried out in a 2% methanol solution using a 1 dm polarimetric tube-result is $(\alpha)_D = -63°$ Elementary analysis gives the following results (%):
C 73.85; H 9.72; N 7.34
For $C_{34}H_{53}N_3O_3$ theoretical % calculated is
C 74.00; H 9.68; N 7.26.

b. The preparation of the salt with methane sulphonic acid from the dihydrolysergyl sphingosine amide is as follows: 1 g of dihydrolysergyl sphingosine amide is dissolved in 50 ml of acetone, and 0.18 g of methane sulphonic acid are added. The solution is then concentrated in small volumes, crystallizing the salt of the dihydrolysergylsphingosine amides with methane sulphonic acid.

Evaluation of the specific rotary power is carried out in a methanol solution of 2% using a 1 dm polarimetric tube-result is $(\alpha)_D = -41.5°$.

EXAMPLE 4

Product 4

Valproylsphingosine amide of the formula:

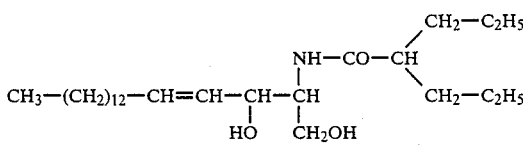

11.5 g of sphinngosine (taken from the sphingolipids present in the bovine brain and corresponding to a sphingosine $C_{18}$) are treated with 1000 ml of absolute ethanol. To this solution 13.1 g of the para-nitrophenylester of valproic acid (prepared according to: Chim. Ther. 3, (5), 336-42, 1968) is added.

This solution is then treated in the manner described in Example 5. The residue is crystallized by tertiarybutyl methyl ether, M.P. 118° C., yield 14.9 g.

Thin layer chromatography (silica gel) utilizing an eluent mixture formed from: methylene chloride (70); ethyl acetate (30);methanol (10); indicates that it is a single compound with Rf 0.85.

Elementary analysis gives the following results (%):
C 73.30; H 12.25; n 3.11
For $C_{26}H_{51}NO_3$ theoretical % calculated is
C 73.36; H 12.08; N 3.29

EXAMPLE 5

Product 5

3,4,5-Trimethoxybenzoylsphingosine amide of the formula:

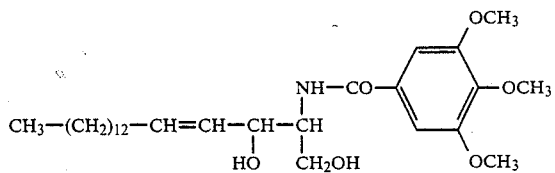

5 g of sphingosine (taken from the sphingolipids present in the bovine brain and corresponding to a sphingosine $C_{18}$) are treated with 500 ml of absolute ethanol. To this solution 7.35 g of a p-nitrophenylester of the 3,4,5-trimethoxybenzoic acid are added (prepared according to: Anales Asoc. Guim. Argentina 26, 51-56, 1938). This mixture is heated and left to precipitate for 2 hours and the solvent is vacuum separated. The residue is mixed with 500 ml of a methylene chloride:ethanol mixture (4:1). The organic solution is washed with an aqueous solution of sodium carbonate and then with water. The organic solution is dried on sodium sulphate, filtered and the solvent is then vacuum separated. The residue crystallizes from tertiarybutyl methyl ether, M.P. 130° C., yield 7.3 g.

Thin layer chromatography (silica gel) using an eluent mixture formed by methylene chloride:ethyl acetate:methanol (40:30:10) indicates that it is a single compound with Rf of 0.5.

Elementary analysis gives the following results (%):
C 68.01; H 9.78; N 2.67
For $C_{28}H_{47}NO_6$ theoretical % is calculated is
C 68.12; H 99.60; N 2.84

EXAMPLE 6

Product 6

Theophyllinacetylsphingosine amide of the formula:

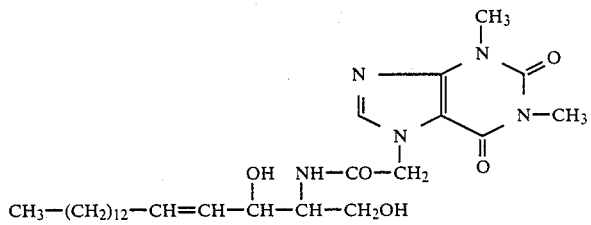

6 g of sphingosine (taken from the sphingolipids present in the bovine brain and corresponding to a sphingosine $C_{18}$) are treated with 500 ml of absolute ethanol. To this solution are added 9.5 g of a p-nitrophenylester of theorphllineacetic acid (prepared according to: Annalen (1976) 860–75). The same procedure as described in Example 5 is then followed.

The residue crystallizes from methanol, M.P. 189° C., yield 8.5 g.

Thin layer chromatography (silica gel) using an eluent mixture formed by methylene chloride:ethyl acetate; methanol (60:30:20), indicates that it is a single compound with Rf of 0.6.

Elementary analysis gives the following results (%): C 62.31; H 8.70; N 13.30

For $C_{27}H_{45}N_5O_5$ theoretical % calculated is C62.40; H 8.73; N 13.48

EXAMPLE 7

Product 7

Nicotinylsphingosine amide of the formula:

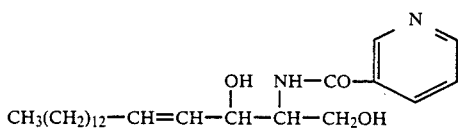

$$CH_3(CH_2)_{12}-CH=CH-\underset{|}{CH}-\underset{|}{CH}-CH_2OH$$
with OH and NH—CO—(pyridyl)

5 g of sphingosine (obtained from the sphingolipids present in the bovine brain and corresponding to a sphingosine $C_{18}$) are treated with 500 ml of absolute ethanol. 5.5 g of p-nitrophenylester of the nicotinic acid are added to the solution (prepared according to: J. Chem. Soc. B (1971) 2401–6). The same procedure as described in Example ;b 5 is then followed.

The residue crystallizes from tertiarybutyl methyl ether, M.P. 105° C., yield 6.7 g.

Thin layer chromatography (silica gel) using an eluent mixture formed by methylene chloride:ethyl acetate:methanol (70:30:10) indicates that it is a single compound with an Rf of 0.23.

Elementary analysis gives the following results (%): C 71.12; H 9.78; N 6.70

For $C_{24}H_{40}N_2O_2$ theoretical % calculated is C71.24; H 9.97; N 6.92

EXAMPLE 8

Product 8

3,4,5-Trimethoxybenzoylpsycosine amide of the formula

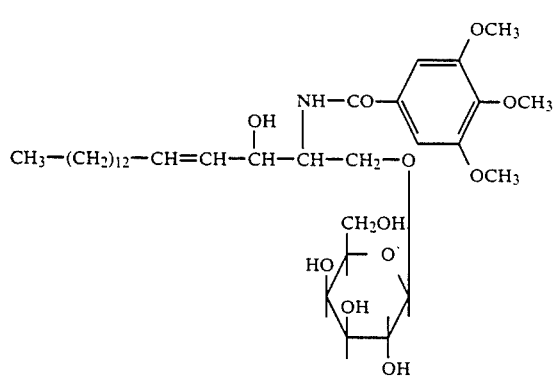

5 g of psycosine (taken from the sphingolipids present in the bovine brain and corresponding to a sphingosine $C_{18}$) are treated with 4.8 g of the p-nitrophenylester of trimethoxybenzoic acid in an ethanolic solution (see Example 5). The same procedure as described in Example 5 is then followed.

The residue crystallizes from ethanol-acetone, M.P. 135° C., yield 6.7 g.

Thin layer chromatography (silica gel) using an eluent mixture formed by chloroform:methanol:water (110:40:6) indicates that it is a single compound with Rf of 0.85.

Elementary analysis gives the following results (%): C 62.02; H 8.54; N 1.99

For $C_{34}H_{57}NO_{11}$ theoretical % calculated is C 62.27; H 8.76; N 2.14

EXAMPLE 9

Product 9

Nicotinylpsycosine amide of the formula

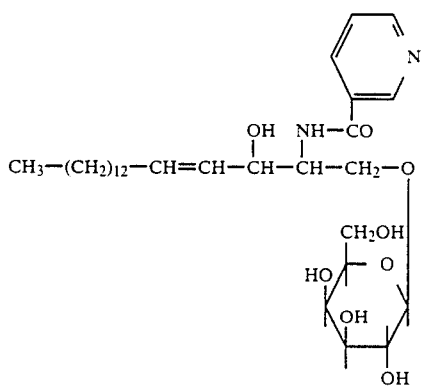

5 g of psycosine (obtained from the sphingolipids present in the bovine brain and corresponding to a sphingosine $C_{18}$) are treated with 3.5 g of the p-nitrophenylester of nicotinic acid in an ethanolic solution (see Example 7). The same procedure as described in Example 5 is then followed.

The residue crystallizes from acetone, M.P. 140° C., yield 6.7 g.

Thin layer chromatography (silica gel) using an eluent mixture formed by chloroform:methanol:water (110:40:6), indicates that it is a single compound with an Rf of 0.80.

Elementary analysis gives the following results (%): C 63.30; H 8.75; N 4.80

For $C_{30}H_{50}N_2O_8$, theoretical % calculated is C 63.58; H 8.80; N 4.94

EXAMPLE 10

Product 10

3,4,5-Trimethoxybenzoyl-sphingosinephosphorylcholine amide of the formula

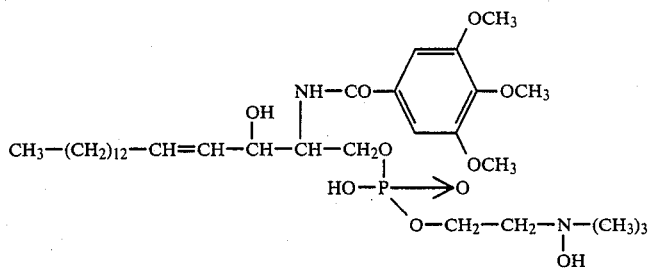

5 g of sphingosinephosphorylcholine (taken from the sphingolipids present in the bovine brain and corresponding to a sphingosine $C_{18}$) are treated with 4.6 g of a p-nitrophenylester of the 3,4,5-trimethoxybenzoic acid in an ethanolic solution (see Example 5).

The same procedure as described in Example 5 is then followed. The residue crystallizes from tertiarybutyl methyl ether, M.P. 127° C., yield 6.1 g.

Thin layer chromatography (silica gel) using an eluent mixture formed by chloroform:methanol:water (60:35:8), indicates that it is a single compound with an Rf of 0.25.

EXAMPLE 11

Product 11

3,4,5-Trimethoxybenzoyl-phosphatidylserine amide of the formula

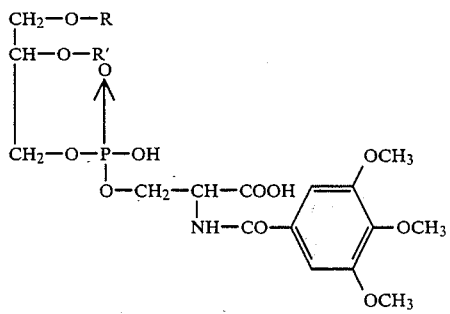

5 g of phosphatidylserine (taken from the phospholipids present in the bovine brain and in which the groups R and R' are mainly stearic, palmitic, oleic, linolenic, linoleic and arachidonic acid residues) are treated with 2.8 g of a p-nitrophenylester of 3,4,5-trimethoxybenzoyl acid in an ethanolic solution (see Example 5). The same procedure as described in Example 5 is then followed, excluding the wash of the organic solution with $Na_2CO_3$. The residue is purified by chromatography, yield 4.5 g.

Thin layer chromatography (silica gel) using an eluent mixture formed by chloroform:methanol:water (70:30:5), indicates that it is a single compound with an Rf of 0.5.

EXAMPLE 12

Product 12

Nicotinylphosphatidylserine amide of the formula

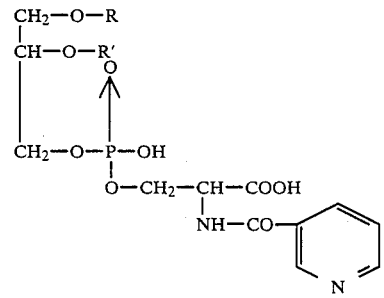

5 g of phosphatidylserine (taken from the phospholipids present in the bovine brain and in which the groups R and R' are mainly stearic, palmitic, oleic, linolenic, linoleic and arachidonic acid residues) are treated with 2 g of a p-nitrophenylester of nicotinic acid in an ethanolic solution (see Example 7).

The same procedure as described in Example 5 is then followed, excluding the wash of the organic solution with $Na_2CO_3$. The residue is purified by chromatography, yield 5.1 g.

Thin layer chromatography (silica gel) using an eluent mixture formed by chloroform:methanol:water (70:35:5), indicates that it is a single compound with an Rf of 0.5.

EXAMPLE 13

Product 13

3,4,5-Trimethoxybenzoyllisophosphatidylserine amide of the formula

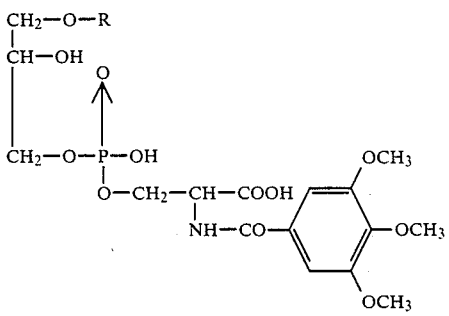

5 g of lisophosphatidylserine (taken from the enzymatic hydrolysis of phosphatidylserine, the R group in the lisophosphatidylserine being mainly stearic or oleic acid) are treated with 4.3 g of a p-nitrophenylester of 3,4,5-trimethoxybenzoyl acid in an ethanolic solution (see Example 5). The same procedure as described in Example 5 is then followed, excluding the wash of the organic solution with Na₂CO₃. The residue is purified by chromatography, yield 6.0 g.

Thin layer chromatography (silica gel) using an eluent mixture formed by chloroform:methanol:water (60:35:8), indicates that it is a single compound with an Rf of 0.3.

EXAMPLE 14

Product 14

3,4,5-Trimethoxybenzoylphosphatidylethanolamine amide of the formula

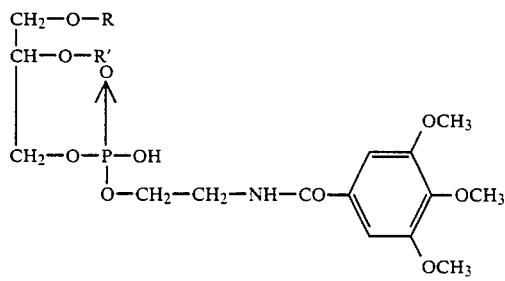

5 g of phosphatidylethanolamine (taken from the phospholipids present in the bovine brain and in which the groups R and R' are mainly oleic, stearic, palmitic, linoleic and arachidonic acid residues) are treated with 3 g of a p-nitrophenylester of 3,4,5-trimethoxybenzoyl acid in an ethanolic solution (see Example 5). The same procedure as described in Example 5 is then followed. The residue is purified by chromatography, yield 5.1 g.

Thin layer chromatography (silica gel) using an eluent mixture formed by methylene chlorine:ethyl acetate:methanol (70:30:20), indicates that it is a single compound with an Rf of 0.30.

EXAMPLE 15

Product 15

Dihydrolysergyldihydrosphingosine amide of the formula

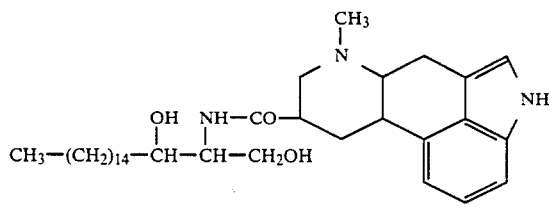

The procedure is carried out as described in Example 3, beginning with 2.5 g of dihydrosphingosine (obtained through the catalytic hydrogenation of the sphingosine C₁₈); 2.24 g of dihydrolysergic acid; 2.24 g of 1-hydroxybenzotriazole; and 2.06 g of dicyclohexyl-carbodiimide. The reaction takes place in chloroform (130 ml). The compound crystallizes from acetone, M.P. 200° C., yield 3.6 g.

Thin layer chromatography (silica gel) using an eluent mixture formed by chloroform:methanol:ammonia 1N (64:24:3.2), indicates that it is a single compound with an Rf of 0.69.

Evaluation of the specific rotary power is carried out in a 2% methanol solution using a 1 dm polarimetric tube. Results: $(\alpha)_D = -47.5°$ Elementary analysis gives the following results (%):
C 73.61; H 10.22; N 7.45
For $C_{34}H_{55}N_3O_3$ theoretical % calculated is
C 73.73; H 10.01; N 7.59

EXAMPLE 16

Product 16

Dihydrolysergylpsychosine amide of the formula

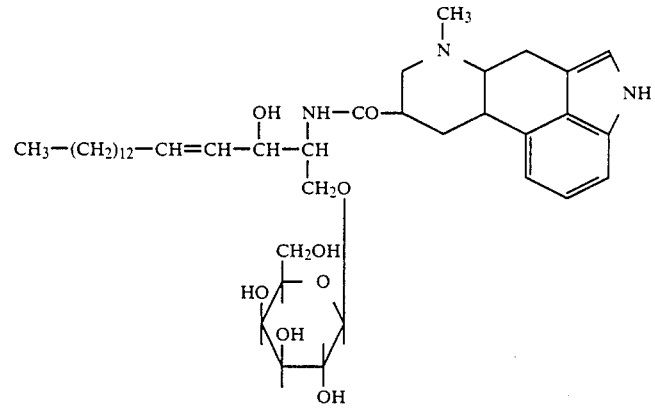

The procedure is carried out as described in Example 3, beginning with 2.8 g of psychosine (obtained from the sphingolipids present in the bovine brain and containing a sphingosinic residue C₁₈); 1.62 g of dihydrolysergic acid; 1.62 g of 1-hydroxybenzotriazole; and 2.06 g of dicyclohexylcarbodiimide. The reaction takes place in a chloroform solution, 100 ml of chloroform. The compound crystallizes from ethyl acetate, M.P. 140° C., yield 3.8 g.

Thin layer chromatography (silica gel) using an eluent mixture formed by chloroform:methanol:ammonia 1N (64:24:3.2), indicates that it is a single compound with an Rf of 0.43.

Evaluation of the specific rotary power is carried out in a 2% methanol solution using a 1 dm polarimetric tube. Results: $(\alpha)_D = -32°$ Elementary analysis gives the following results (%):
C 67.01; H 8.62; N 5.48
For $C_{40}H_{63}N_3O_8$, theoretical % calculated is
C 67.29; H 8.89; N 5.89

EXAMPLE 17

Products 17.1 and 17.2

Isolysergylpsychosine amide of the formula

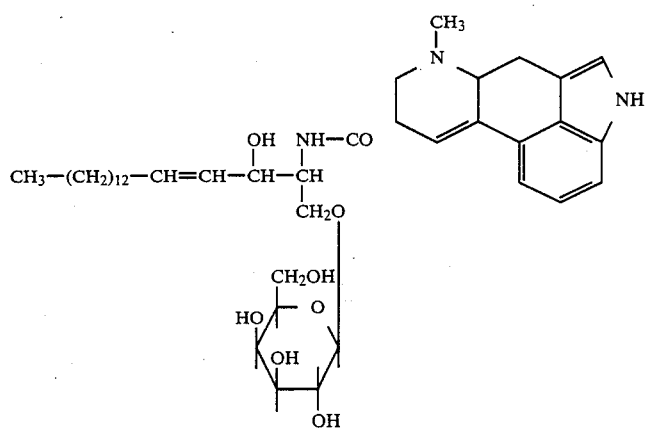
(Product 17.1)

and lysergylpsychosine amide of the formula

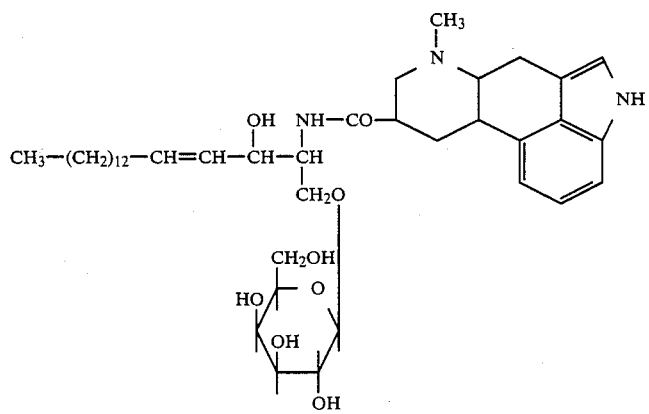
(Product 17.2)

The procedure is carried out as described in Example 2, beginning with 6.7 g of D-lysergic acid; 4.45 g of N-N'-carbonyldimidazole; 12.7 g of psychosine (taken from sphingolipids present in the bovine brain and containing a sphingosinic residue $C_{18}$). The reaction takes place in a dimethylformamide solution of the same volume as described in Example 2. The residue is then chromatographically fractionated, separating the two compounds: Product 17.1 and Product 17.2.

a. Product 17.1—isolysergyl psychosine amide, M.P. 97°–100° C.

Chromatography on silica gel using an eluent mixture formed by chloroform: methanol: ammonia 1M (64:24:3.2), indicates that it is a single compound with Rf 0.76.

Evaluation of the specific rotary power is carried out in a 2% methanol solution using a 1 dm polarimetric tube. Results: $(\alpha)_D = +143°$ Elementary analysis gives the following results (%):
C 67.35; H 8.51; N 5.65

For $C_{40}H_{61}N_3O_8$ theoretical % calculated is
C 677.48; H 8.64; N 5.90 b. Product 17.2—lysergylpsychosine amide, M.P. 122°–126° C.

Chromatography on silica gel using an eluent mixture formed by chloroform:methanol:ammonia 1M (64:24:3.2), indicates that it is a single compound with an Rf of 0.59.

Evaluation of the specific rotary power is carried out in a 2% methanol solution using a 1 dm polarimetric tube. Results: $(\alpha)_D = +2°$ Elementary analysis gives the following results (%):
C 67.40; H 8.56; N 5.71

For $C_{40}H_{61}N_3O_8$ theoretical % calculated is
C 67.48; H 8.64; N 5.90

EXAMPLE 18

Product 18

Isonicotinylsphingosine amide of the formula

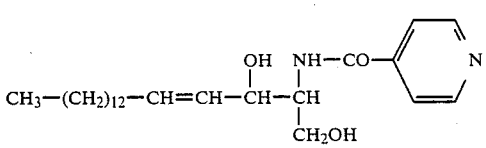

5 g of sphingosine (taken from the sphingolipids present in the bovine brain and corresponding to a sphingosine $C_{18}$) are treated with 500 ml absolute ethanol. To the solution, 5.5 g of the p-nitrophenylester of isonicotinic acid (prepared according to: C.A. 59, 8708b (1963)) is added. The same procedure as described in Example 5 is then followed. The residue crystallizes from acetonitrile, M.P. 116° C., yield 6.0 g.

Thin layer chromatography (silica gel) using an eluent mixture formed by methylene chloride: ethyl acetate: methanol (70:30:15), indicates that it is a single compound with an Rf of 0.49.

Elementary analysis gives the following results (%):
C 71.12; H 9.78; N 6.70
For $C_{24}H_{40}N_2O_3$ theoretical % calculated is
C 71.24; H 9.97; N 6.92

PHARMACOLOGICAL PROPERTIES

The compounds described above in Examples 1, 2, 3, 15 and 16 were tested for pharmacological activity. These compounds were tested both in vitro and in vivo in laboratory animals and proved to be capable of acting directly on the central nervous system.

Product 1 from Example 1—Gamma-aminobutyrylsphingosine amide a. in vitro tests

Gamma-aminobutyric acid (GABA), $NH_2(CH_3)_3-CO_2H$, is an endogenous substance and is biologically active due to interaction with a specific receptor but is incapable, by itself, of penetrating the encephalic barrier. Accordingly, GABA has been found to be active in vitro but relatively inactive in vivo. The compounds of the present invention, on the other hand, are active both in vitro and in vivo. To show this activity of the compounds of the present invention, in vitro tests measuring the binding levels of radioactive gamma-aminobutyric acid, $^3H$-GABA, on synaptic membranes of the rat cortex were carried out according to the method of Enna and Snyder (Enna, S. J. and Synder, S. H., Mol. Pharmacol. 13, 442-45300; (1977)).

Table I presents the results of these tests, expressed in percentage of the fixed active product, comparing the in vitro activity of Product 1 with the activities of the individual components which comprise Product 1. The results show that sphingosine alone exhibits no biological activity while GABA alone exhibits activity comparable to that of Product 1.

TABLE I

Product 1
Binding on rat cortex membranes

| Product utilized | | Product bound % |
|---|---|---|
| $^3H$—GABA $2.10^{-8}$ M | | 100 |
| $^3H$—GABA $2.10^{-8}$ M | + GABA $10^{-8}$ M | 90 |
| | + GABA $10^{-7}$ M | 45 |
| | + GABA $10^{-6}$ M | 25 |
| | + GABA $10^{-5}$ M | 20 |
| | + GABA $10^{-4}$ M | 20 |
| $^3H$—GABA $2.10^{-8}$ M | + sphingosine $10^{-8}$ M | 100 |
| | + sphingosine $10^{-7}$ M | 100 |
| | + sphingosine $10^{-6}$ M | 100 |
| | + sphingosine $10^{-5}$ M | 100 |
| | + sphingosine $10^{-4}$ M | 100 |
| $^3H$—GABA $2.10^{-8}$ M | + product 1 $10^{-8}$ M | 95 |
| | + product 1 $10^{-7}$ M | 60 |
| | + product 1 $10^{-6}$ M | 40 |
| | + product 1 $10^{-5}$ M | 25 |
| | + product 1 $10^{-4}$ M | 20 | b. in vivo tests

The in vivo activity of Product 1 was measured by the method described by Costa et al (E. Costa, A. Guidotti and C. C. Mao; "Evidence for involvement of GABA in the Action of Benzodiazepines: Studies in Rat Cerebellum" in *Mechanism of Action of Benzodiazepines;* Ed. by E. Costa and P. Greengard, New York, Raven Press. pp. 113-130 (1975)) and by Loescher and Frey (Loesher, W. and Frey, H. H.; "Effect of convulsant and anticonvulsant agents on level and metabolism of gamma-aminobutyric acid in mouse brain"; Naunyn-Schmiedeberg's Arch. Pharmacol. 296, 263-269 (1977)). These tests are based on the known activity of isoniazide to cause convulsions and a lowering of the GABA cerebral levels and the glutamicdecarboxylase enzyme activity. According to the test method, isoniazide is administered to the control animals (rats) while isoniazide and the appropriate test compound are administered to the groups of test animals and the results are measured in terms of the number of animals exhibiting convulsions, the latency of convulsions and the number of deaths. The results are presented in Table II and show that Product 1 has far superior in vivo activity as compared to GABA or sphingosine alone.

TABLE II

Product 1
Anticonvulsivant effects in rat

| | Isoniazide 160 mg/kg (s.c.) | Isoniazide 160 mg/kg (s.c.) + GABA 8 mg/kg (i.p.) | Isoniazide 160 mg/kg (s.c.) + Sphingosine 12 mg/kg (i.p.) | Isoniazide 160 mg/kg (s.c.) + Product 1 20 mg/kg (i.p.) |
|---|---|---|---|---|
| Number of animals in convulsions | 26/30 | 24/30 | 20/30 | 9/30 |
| Latency of the convulsions measured in seconds | 3070 ± 110 | 3100 ± 156 | 3700 ± 200 | 4500 ± 330 |
| Number of dead animals | 15 | 14 | 9 | 3 |

Product 3 of Example 3—Dihydrolysergylsphingosine amide a. in vitro tests

The in vitro biological activity was determined by comparative tests measuring the binding power of the labelled spiroperidole ($^3H$)-spiroperidole on hypophysis sinaptosomal rat membranes according to the method described by Greese et al (GREESE I., SCHNEIDER R. and SNYDER S. H.; H-spiroperidole labels dopamine receptors in pituitary and brain; Europ. J. Pharmacol. 46, 377-381 (1977)).

The results obtained and illustrated in Table III show that the binding power of Product 3 is significant and far superior, under the same experimental conditions, to that of dihydrolysergic acid or sphingosine alone.

TABLE III

Product 3
Binding to hypophysis membranes of rat

| Product utilized | | Product bound % |
|---|---|---|
| ($^3H$) spiroperidole $2.10^{-9}$ M (Control) | | 100 |
| ($^3H$) spiroperidole $2.10^{-9}$ M + dihydrolysergic acid | $10^{-7}$ M | 100 |
| | $10^{-6}$ M | 100 |
| | $10^{-5}$ M | 95 |
| | $10^{-4}$ M | 45 |
| ($^3H$) spiroperidole $2.10^{-9}$ M + sphingosine | $10^{-7}$ M | 100 |
| | $10^{-6}$ M | 100 |
| | $10^{-5}$ M | 100 |

TABLE III-continued

Product 3
Binding to hypophysis membranes of rat

| Product utilized | Product bound % | |
|---|---|---|
| ($^3$H) spiroperidole $2.10^{-9}$ M + Product 3 | $10^{-4}$ M | 100 |
| | $10^{-7}$ M | 100 |
| | $10^{-6}$ M | 90 |
| | $10^{-5}$ M | 40 |
| | $10^{-4}$ M | 10 | b. in vivo tests

The in vivo biological activity of Product 3 was measured by evaluating the serum levels of prolactin in hyperprolactinemic animals according to the RIA method (radioimmunoassay) and the instructions in the NIAMDD program. The results obtained and illustrated in Table IV, expressed as % of inhibition, show that Product 3 exhibits significant biological activity, especially as compared to the weak effect of dihydrolysergic acid.

TABLE IV

Product 3
Hypoprolactinemic effect in rats

| Product utilized | Prolactin ng/ml | Inhibition % |
|---|---|---|
| Control at the circadian peak at 4 p.m. | 68.0 ± 5.4 | 0 |
| Dihydrolysergic acid | | |
| 0.5 mg/kg | 60.0 ± 3.2 | 0 |
| 5.0 mg/kg | 51.0 ± 6.7 | 25 |
| Sphingosine | | |
| 0.5 mg/kg | 71.0 ± 4.2 | 0 |
| 5.0 mg/kg | 62.0 ± 6.8 | 0 |
| Product 3 | | |
| 0.5 mg/kg | 38.7 ± 4.7 | 42 |
| 5.0 mg/kg | 32.2 ± 5.7 | 52 |
| Control | | |
| Sulpiride 10 γ/kg | 77.0 ± 9.0 | 0 |
| Sulpiride + Dihydrolysergic acid | | |
| 0.5 mg/kg | 66.0 ± 2.8 | 0 |
| 5.0 mg/kg | 65.0 ± 4.6 | 0 |
| Sulpiride + sphingosine | | |
| 0.5 mg/kg | 72.0 ± 4.5 | 0 |
| 5.0 mg/kg | 77.0 ± 8.7 | 0 |
| Sulpiride + product 3 | | |
| 0.5 mg/kg | 53.7 ± 8.5 | 30 |
| 5.0 mg/kg | 31.2 ± 2.5 | 60 |

Product 15 of Example 15—Dihydrolysergyldihydrosphingosine amide

The in vitro biological activity and in vivo activities of Product 15 were evaluated according to the same methods as used above for Product 3 of Example 3.

The results obtained and presented in Tables V and VI show the in vitro and in vivo activities of Product 15 to be far superior to either dihydrolysergic acid or dihydrosphingosine alone.

TABLE V

Product 15
Binding to hypophysis membranes of rat

| Product utilized | Product | bound % |
|---|---|---|
| ($^3$H) spiroperidole 2 nM (Control) | | 100 |
| ($^3$H) spriroperidole 2 nM + dihydrolysergic acid | $10^{-7}$ M | 100 |
| | $10^{-6}$ M | 100 |
| | $10^{-5}$ M | 95 |
| | $10^{-4}$ M | 45 |

TABLE V-continued

Product 15
Binding to hypophysis membranes of rat

| Product utilized | Product | bound % |
|---|---|---|
| ($^3$H) spiroperidole 2 nM + dihydrosphingosine | $10^{-7}$ M | 100 |
| | $10^{-6}$ M | 100 |
| | $10^{-5}$ M | 100 |
| | $10^{-4}$ M | 100 |
| ($^3$H) spiroperidole 2 nM + Product 15 | $10^{-7}$ M | 100 |
| | $10^{-6}$ M | 90 |
| | $10^{-5}$ M | 30 |
| | $10^{-4}$ M | 20 |

TABLE VI

Product 15
Hypoprolactinemic effect in rat

| Product utilized | Prolactin ng/ml | Inhibition % |
|---|---|---|
| Control at the circadian peak at 4 p.m. | 62.0 ± 3.8 | 0 |
| Dihydrolysergic acid | | |
| 0.5 mg/kg | 60.0 ± 4.1 | 0 |
| 5.0 mg/kg | 48.0 ± 5.1 | 23 |
| Dihydrosphingosine | | |
| 0.5 mg/kg | 66.0 ± 4.2 | 0 |
| 5.0 mg/kg | 60.0 ± 2.8 | 0 |
| Product 15 | | |
| 0.5 mg/kg | 40.0 ± 5.6 | 35 |
| 5.0 mg/kg | 31.0 ± 3.4 | 50 |
| Control | | |
| Sulpiride 10 γ/kg | 85.0 ± 9.0 | 0 |
| Sulpiride + Dihydrolysergic acid | | |
| 10 γ/kg + 0.5 mg/kg | 77.0 ± 5.0 | 0 |
| 10 γ/kg + 5.0 mg/kg | 76.0 ± 8.0 | 0 |
| Sulpiride + dihydrosphingosine | | |
| 10 γ/kg + 0.5 mg/kg | 81.0 ± 11.0 | 0 |
| 10 γ/kg + 5.0 mg/kg | 74.0 ± 6.0 | 0 |
| Sulpiride + product 15 | | |
| 10 γ/kg + 0.5 mg/kg | 48.0 ± 4.0 | 44 |
| 10 γ/kg + 5.0 mg/kg | 39.0 ± 6.0 | 55 |

Product 2.2 of Example 2—Lysergylsphingosine amide

The in vitro and in vivo biological activities of Product 2.2 were evaluated according to the same methods as described above for Product 3, Example 3.

The results obtained and presented in Tables VII and VIII show the in vitro and in vivo activities of Product 2.2 to be far superior to either lysergic acid or sphingosine alone.

TABLE VII

Product 2.2
Binding to hypophysis membranes of rats

| Product utilized | Product | bound % |
|---|---|---|
| ($^3$H) spiroperidole 2 nM (Control) | | 100 |
| ($^3$H) spiroperidole 2 nM + lysergic acid | $10^{-7}$ M | 100 |
| | $10^{-6}$ M | 100 |
| | $10^{-5}$ M | 90 |
| | $10^{-4}$ M | 60 |
| ($^3$H) spiroperidole 2 nM + sphingosine | $10^{-7}$ M | 100 |
| | $10^{-6}$ M | 100 |
| | $10^{-5}$ M | 100 |
| | $10^{-4}$ M | 100 |
| ($^3$H) spiroperidole 2 nM + product 2.2 | $10^{-7}$ M | 100 |
| | $10^{-6}$ M | 85 |
| | $10^{-5}$ M | 55 |
| | $10^{-4}$ M | 35 |

TABLE VIII
Product 2.2
Hypoprolactinemic effect in rats

| Product utilized | Prolactin ng/ml | Inhibition % |
|---|---|---|
| Control at the circadian peak at 4 p.m. | 65.0 ± 4.8 | 0 |
| Lysergic acid | | |
| 0.5 mg/kg | 61.0 ± 3.8 | 0 |
| 5.0 mg/kg | 52.0 ± 6.2 | 20 |
| Sphingosine | | |
| 0.5 mg/kg | 68.0 ± 6.0 | 0 |
| 5.0 mg/kg | 61.0 ± 8.0 | 0 |
| Product 2.2 | | |
| 0.5 mg/kg | 48.0 ± 4.8 | 27 |
| 5.0 mg/kg | 40.0 ± 2.6 | 39 |
| Control | | |
| Sulpiride 10 γ/kg | 87.0 ± 8.7 | 0 |
| Sulpiride + Lysergic acid | | |
| 10 γ/kg + 0.5 mg/kg | 76.0 ± 9.0 | 13 |
| 10 γ/kg + 5.0 mg/kg | 73.0 ± 10.0 | 16 |
| Sulpiride + Sphingosine | | |
| 10 γ/kg + 0.5 mg/kg | 81.0 ± 11.0 | 0 |
| 10 γ/kg + 5.0 mg/kg | 74.0 ± 6.0 | 14 |
| Sulpiride + product 2.2 | | |
| 10 γ/kg + 0.5 mg/kg | 59.0 ± 6.0 | 32 |
| 10 γ/kg + 5.0 mg/kg | 49.0 ± 5.0 | 44 |

Product 16 of Example 16—Dihydrolisergylpsychosine amide

The in vitro and in vivo biological activities of Product 16 were evaluated according to the same methods as described for Product 3, Example 3.

The results obtained and presented in Tables IX and X show the in vitro and in vivo activities of Product 16 to be far superior to either dihydrolysergic acid or psychosine alone.

TABLE IX
Product 16
Binding to hypophysis membranes of rats

| Product utilized | Product | bound % |
|---|---|---|
| ($^3$H) spiroperidole 2 nM (Control) | | 100 |
| ($^3$H) spiroperidole 2 nM + dihydrolysergic acid | $10^{-7}$ M | 100 |
| | $10^{-6}$ M | 100 |
| | $10^{-5}$ M | 90 |
| | $10^{-4}$ M | 60 |
| ($^3$H) spiroperidole 2 nM + psychosine | $10^{-7}$ M | 100 |
| | $10^{-6}$ M | 100 |
| | $10^{-5}$ M | 90 |
| | $10^{-4}$ M | 60 |
| ($^3$H) spiroperidole 2 nM + product 16 | $10^{-7}$ M | 100 |
| | $10^{-6}$ M | 80 |
| | $10^{-5}$ M | 45 |
| | $10^{-4}$ M | 25 |

TABLE X
Product 16
Hypoprolactinemic effect in rats

| Product utilized | Prolactin ng/ml | Inhibition % |
|---|---|---|
| Control at the circadian peak at 4 p.m. | 58.0 ± 6.0 | 0 |
| Dihydrolysergic acid | | |
| 0.5 mg/kg | 57.0 ± 5.0 | 0 |
| 5.0 mg/kg | 49.0 ± 6.0 | 16 |
| Psychosine | | |
| 0.5 mg/kg | 50.0 ± 5.0 | 14 |
| 5.0 mg/kg | 41.0 ± 5.0 | 30 |
| Product 16 | | |
| 0.5 mg/kg | 40.0 ± 7.0 | 31 |
| 5.0 mg/kg | 31.0 ± 6.0 | 47 |
| Control | | |
| Sulpiride 10 γ/kg | 81.0 ± 9.0 | 0 |
| Sulpiride + Dihydrolysergic acid | | |
| 10 γ/kg + 0.5 mg/kg | 77.0 ± 6.0 | 0 |
| 10 γ/kg + 5.0 mg/kg | 70.0 ± 4.0 | 14 |
| Sulpiride + psychosine | | |
| 10 γ/kg + 0.5 mg/kg | 70.0 ± 6.0 | 14 |
| 10 γ/kg + 5.0 mg/kg | 61.0 ± 7.0 | 25 |
| Sulpiride + product 16 | | |
| 10 γ/kg + 0.5 mg/kg | 51.0 ± 7.0 | 37 |
| 10 γ/kg + 5.0 mg/kg | 39.0 ± 4.0 | 52 |

THERAPEUTIC USES

According to the present invention, the organic amides derived from nitrogenous lipids can be used as medicaments for various therapeutic uses, in particular for those uses corresponding to the activities of the active acids from which the amides are prepared. For example, derivatives of lysergic, isolysergic, dihydrolysergic, 2-bromo-lysergic, 2-bromo-dihydrolysergic, 1-methyl-lysergic, 1-methyl-dihydrolysergic, 1-methyl-2-bromo-lysergic, 1-methyl-2-bromo-dihydrolysergic, gamma-amino-butyric, valproic, trimethoxybenzoic and nicotinic acid are suitable for use as medicaments capable of exhibiting pharmacological activity on the central nervous system (CNS). The derivatives of lysergic acid, 2-bromo-lysergic, 1-methyl-lysergic and 1-methyl-2-bromo-lysergic also exert a significant activity on the uterus. Specifically, the compounds of the present invention which are experimentally active against isoniazid convulsions and on the binding of GABA in vitro, and the pharmaceutical compositions containing them, may be therapeutically useful in pathologies connected with changes in the function of the GABAurgic system, since these products are able to enhance levels of GABA in the central nervous system (CNS) and in the specific cerebral areas, thereby enabling the GABA, bound to natural amino-alcohols, to penetrate the blood-brain barrier. To be more precise, these compounds and the pharmaceutical preparations containing them may be usefully employed in the prevention of convulsive states which usually give rise to tonoclonic contractions and/or loss of consciousness, as in epilepsy; that is, in focal epilepsy, in psychomotorial epilepsy, in major epilepsy, in idiopahtic epilepsy, in status epilipticus and in centroencaphalic epilepsy (in minor epilepsy, akinetic attacks, mioclonic epilepsy) and in general, in pathologies deriving from decrease of inhibitory control in the CNS.

The compounds which have proved to be active in inhibiting the serum levels of prolactin and in the binding in vitro of the dopaminergic ligand in the hypophysis, and the pharmaceutical compositions deriving from them, as exemplified in the in vivo and in vitro data noted above, may be usefully employed in pathologies which present alterations in the release of neuropeptides from hypophysis as prolactin due to changes in the regulation of the neurotransmittor systems with loss of dopaminergic system tonic inhibition or, in general, of the hypothalamic routes as in hyperprolactinemias caused by neuroleptics such as sulpiride, chlorpromazine, etc.

Thus, the drugs deriving from the compounds of the present invention may be used in the treatment of behavioral alterations resulting from modifications of neuropeptide hormones from hypophysis as hyperprolactinemic syndromes with loss of lipids and impotence, and hypopituitarism with changes in personality, apathy, indifference, astenia, loss of libido and confusion, and premenstrual syndromes with depression and changes of mood and climacteric syndromes with variations in mood, irritability, anxiety, nervousness and depression.

The compounds of the present invention can be administered as pharmaceutical compositions containing, as an active ingredient, one or more of the amides in association with one or more compatible and pharmaceutically acceptable excipients. The compositions can be administered via various administration routes, such as injectable solutions, tablets, gelatine capsules and suppositories. The dosage administered will vary depending upon the desired effect and administration route, but, for example, in oral administration the dosages can be between 10 and 300 mg of active substance per day with a single dosage of from 10 to 100 mg.

The following are examples of pharmaceutical compositions for oral administration:

a. Pharmaceutical preparation 1: 10 mg tablets
 Each tablet contains:
  Active substance: 10 mg
  Microcrystalline cellulose: 100 mg
  Lactose: 150 mg
  Magnesium stearate: 2.5 mg
  Starch: 20 mg b. Pharmaceutical preparation 2: 50 mg tablets
 Each tablet contains:
  Active substance: 50 mg
  Microcrystalline cellulose: 100 mg
  Lactose: 110 mg
  Magnesium stearate: 2.5 mg
  Starch: 20 mg c. Pharmaceutical preparation 3: 100 mg tablets
 Each tablet contains:
  Active substance: 100 mg
  Microcrystalline cellulose: 100 mg
  Lactose: 2.5 mg
  Magnesium stearate: 3.5 mg
  Starch: 25 mg d. Pharmaceutical preparation 4: 10 mg gelatine capsule
 Each capsule contains:
  Active substance: 10 mg
  Vegetable oil: 100 mg
  Gelatine: 100 mg
  Glycerine: 25 mg e. Pharmaceutical preparation 5: 50 mg gelatine capsule
 Each capsule contains:
  Active substance: 50 mg
  Vegetable oil: 120 mg
  Gelatine: 110 mg
  Glycerine: 30 mg f. Pharmaceutical preparation 6: 100 mg gelatine capsule
 Each capsule contains:
  Active substance: 100 mg
  Vegetable oil: 150 mg
  Gelatine: 130 mg
  Glycerine: 44 mg

We claim:

1. An organic amide compound of the formula:

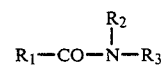

wherein $R_1$—CO is a residue of a carboxylic acid which has biological or pharmaceutical activity, with the proviso that the carboxylic acid is not a natural fatty acid normally bound to nitrogen of nitrogenous lipids, $R_2$ is a hydrogen atom, a saturated $C_{1-7}$ alkyl group or a saturated $C_{4-7}$ cycloalkyl group, and $R_3N$ is a residue of a phospholipid or sphingolipid, or a pharmaceutically acceptable salt thereof.

2. An organic amide compound of the formula:

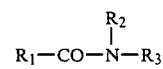

wherein $R_1$—CO is an acyl residue or theophyllineacetic acid, $R_2$ is a hydrogen atom and $R_3$ is a residue of a phospholipid having the chemical structure:

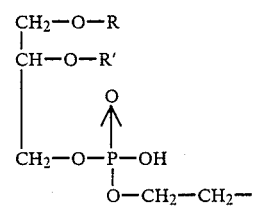

wherein R and R' each represent a hydrogen atom or an acyl residue of a member selected from the group consisting of stearic, palmitic, oleic, linolenic, linoleic and arachidonic acid, or a pharmaceutically acceptable salt thereof.

3. An organic amide compound of the formula:

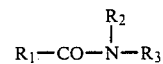

wherein $R_1$—CO is an acyl residue of theophyllineacetic acid, $R_2$ is a hydrogen atom and $R_3$ is a residue of a phospholipid having the chemical structure:

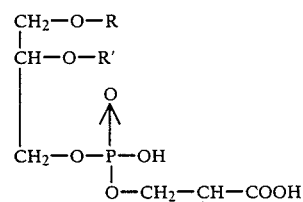

wherein R and R' each represent a hydrogen atom or an acyl residue of a member selected from the group consisting of stearic, palmitic, oleic, linolenic, linoleic and arachidonic acid, or a pharmaceutically acceptable salt thereof.

4. An organic amide compound of the formula:

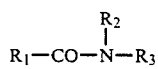

wherein $R_1$—CO is an acyl residue of a theophyllineacetic acid, $R_2$ is a hydrogen atom and $R_3$ is a residue of a sphingolipid having a chemical structure selected from the group consisting of:

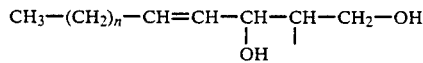

wherein n is from 6 to 16,

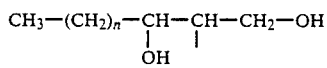

wherein n is from 8 to 18,

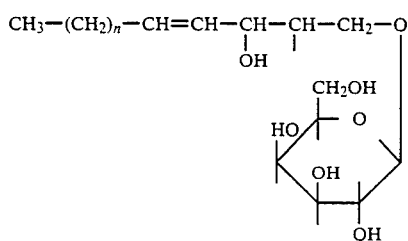

wherein n is from 6 to 16,

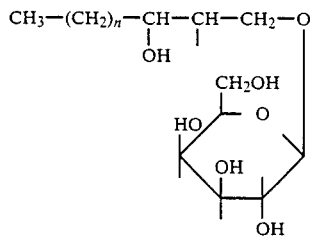

wherein n is from 8 to 18,

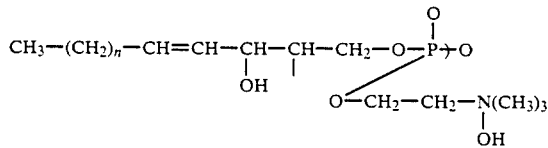

wherein n is from 6 to 16,

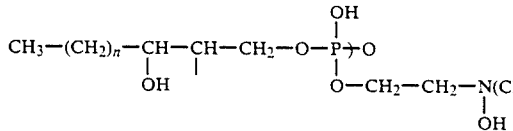

wherein n is from 8 to 18, and

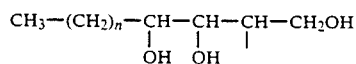

wherein n is from 11 to 15,
or a pharmaceutically acceptable salt thereof.

5. An organic amide compound according to claim 4, wherein $R_3$ represents the residue of a sphingolipid having the chemical structure:

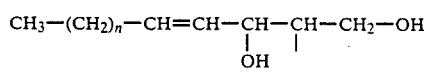

wherein n is from 6 to 16.

6. An organic amide compound according to claim 4, wherein $R_3$ represents the residue of a sphingolipid having the chemical structure:

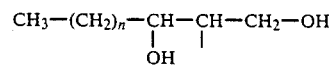

wherein n is from 8 to 18.

7. An organic amide compound according to claim 4, wherein $R_3$ represents the residue of a sphingolipid having the chemical structure:

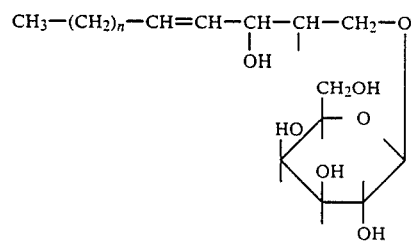

wherein n is from 6 to 16.

8. An organic amide compound according to claim 4, wherein $R_3$ represents the residue of a sphingolipid having the chemical structure:

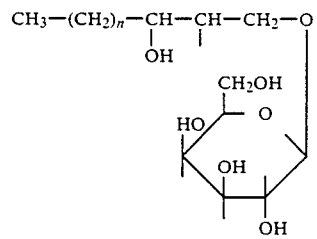

wherein n is from 8 to 18.

9. An organic amide compound according to claim 4, wherein $R_3$ represents the residue of a sphingolipid having the chemical structure:

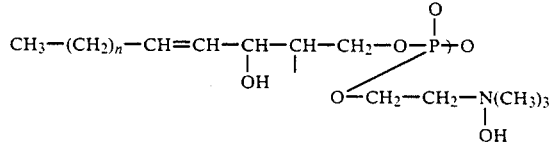

wherein n is from 6 to 16.

10. An organic amide compound according to claim 4, wherein $R_3$ represents the residue of a sphingolipid having the chemical structure:

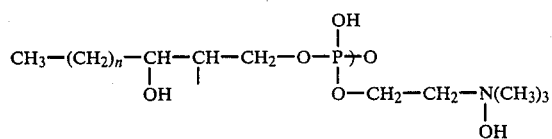

wherein n is from 8 to 18.

11. An organic amide compound according to claim 4, wherein $R_3$ represents the residue of a sphingolipid having the chemical structure:

$$CH_3-(CH_2)_n-CH-CH-CH-CH_2-OH$$
$$\quad\quad\quad\quad\quad\;\; |\quad\;\; |\quad\;\; |$$
$$\quad\quad\quad\quad\quad\;\; OH\;\; OH$$

wherein n is from 11 to 15.

12. A pharmaceutical composition useful for treating disorders of the central and peripheral nervous systems comprising an effective amount of an organic amide compound according to claim 2, 3, 4, 5, 6, 7, 8, 9, 10, 11, or a pharmaceutically acceptable salt thereof, in combination with a pharmaceutically acceptable carrier or diluent.

13. A pharmaceutical composition according to claim 12, wherein said composition is in oral dosage form containing from 10 to 100 mg. of said organic amide compound.

* * * * *